United States Patent
Lefebvre

(10) Patent No.: US 8,075,483 B2
(45) Date of Patent: Dec. 13, 2011

(54) DEVICE FOR USE IN MEASURING AND/OR ANALYSING AT LEAST ONE PARAMETER OF AN EXTERNAL BODY PORTION

(75) Inventor: Marc André Lefebvre, Lusignan (FR)

(73) Assignee: L'Oréal S.A., Paris (FR)

( * ) Notice: Subject to any disclaimer, the term of this patent is extended or adjusted under 35 U.S.C. 154(b) by 1117 days.

(21) Appl. No.: 10/494,422

(22) PCT Filed: Oct. 31, 2002

(86) PCT No.: PCT/EP02/13201
§ 371 (c)(1), (2), (4) Date: May 5, 2004

(87) PCT Pub. No.: WO03/039373
PCT Pub. Date: May 15, 2003

(65) Prior Publication Data
US 2004/0254546 A1    Dec. 16, 2004

Related U.S. Application Data

(60) Provisional application No. 60/331,003, filed on Nov. 6, 2001.

(30) Foreign Application Priority Data

Nov. 6, 2001    (FR) ...................................... 01 14334

(51) Int. Cl.
*A61B 5/00* (2006.01)
(52) U.S. Cl. ........................................................ 600/300
(58) Field of Classification Search ............. 33/485–494
See application file for complete search history.

(56) References Cited

U.S. PATENT DOCUMENTS

| | | | | |
|---|---|---|---|---|
| 422,701 | A | * | 3/1890 | Benzinger ........................ 33/485 |
| 1,643,295 | A | * | 9/1927 | Crump .......................... 132/75.4 |
| 1,838,616 | A | * | 12/1931 | Glancy ............................ 33/1 N |

(Continued)

FOREIGN PATENT DOCUMENTS

FR    2 368 708    5/1978

(Continued)

OTHER PUBLICATIONS

English language Derwent Abstract of FR 2 368 708, May 19, 1978.

(Continued)

*Primary Examiner* — Charles A Marmor, II
*Assistant Examiner* — Karen Toth
(74) *Attorney, Agent, or Firm* — Finnegan, Henderson, Farabow, Garrett & Dunner, L.L.P.

(57) ABSTRACT

A device (1) for use in measuring and/or analyzing at least one parameter of an external portion of a body comprises at least one surface (3) configured to be placed in the vicinity of said external portion. The device is either a) configured to be able to be modeled over said external portion and made of a material comprising inorganic material, or b) configured to not be able to be modeled over said external portion and made essentially of at least, one inorganic material. When the device (1) is configured to not be able to be modeled, and when material defining the surface (3) is not in at least one of a fibrous form and a particulate form, the surface comprises an inorganic material other than glass.

5 Claims, 2 Drawing Sheets

U.S. PATENT DOCUMENTS

| | | | | |
|---|---|---|---|---|
| 2,002,580 A | * | 5/1935 | MacDonald | 12/146 L |
| 2,067,567 A | * | 1/1937 | Gruca | 602/20 |
| 2,289,823 A | * | 7/1942 | Bradshaw | 12/146 M |
| 2,307,892 A | * | 1/1943 | Lowther | 33/382 |
| 2,562,348 A | * | 7/1951 | Bowser, Jr. | 33/492 |
| 3,825,017 A | * | 7/1974 | Scrima | 36/181 |
| 4,541,443 A | * | 9/1985 | Brothers et al. | 132/75.6 |
| 4,682,608 A | * | 7/1987 | De Rigal et al. | 600/587 |
| 4,819,645 A | | 4/1989 | Peck | |
| 4,865,038 A | * | 9/1989 | Rich et al. | 600/344 |
| 4,976,272 A | * | 12/1990 | Bazin et al. | 600/587 |
| 5,094,248 A | * | 3/1992 | Kawam | 600/572 |
| 5,154,173 A | * | 10/1992 | Aultman | 36/154 |
| 5,242,304 A | * | 9/1993 | Truax et al. | 433/177 |
| 5,270,168 A | * | 12/1993 | Grinnell | 435/7.21 |
| 5,382,189 A | * | 1/1995 | Arendall | 451/557 |
| 5,433,214 A | | 7/1995 | Brehm et al. | |
| 5,438,984 A | * | 8/1995 | Schoendorfer | 600/573 |
| 5,478,235 A | * | 12/1995 | Schuldt et al. | 433/37 |
| 5,503,552 A | * | 4/1996 | Diesso | 433/37 |
| 5,582,517 A | * | 12/1996 | Adell | 433/6 |
| 5,638,815 A | * | 6/1997 | Schoendorfer | 600/346 |
| D409,336 S | * | 5/1999 | Stein | D28/63 |
| 5,958,339 A | | 9/1999 | Belly et al. | |
| 6,010,336 A | * | 1/2000 | Shimotoso et al. | 433/201.1 |
| 6,036,659 A | * | 3/2000 | Ray et al. | 600/573 |
| 6,226,811 B1 | * | 5/2001 | Fagan | 4/606 |
| 6,961,490 B2 | * | 11/2005 | Maisenhoelder et al. | 385/37 |
| 7,344,499 B1 | * | 3/2008 | Prausnitz et al. | 600/309 |
| 2002/0002328 A1 | * | 1/2002 | Tamada | 600/347 |
| 2002/0082499 A1 | * | 6/2002 | Jacobsen et al. | 600/439 |
| 2002/0099356 A1 | * | 7/2002 | Unger et al. | 604/501 |
| 2003/0045799 A1 | * | 3/2003 | Bazin et al. | 600/476 |
| 2003/0050561 A1 | * | 3/2003 | Bazin et al. | 600/476 |
| 2003/0135167 A1 | * | 7/2003 | Gonnelli | 604/272 |
| 2003/0199905 A1 | * | 10/2003 | Boecker et al. | 606/181 |
| 2004/0225215 A1 | * | 11/2004 | Querleux et al. | 600/437 |
| 2006/0178904 A1 | * | 8/2006 | Aghassian et al. | 705/1 |
| 2006/0210154 A1 | * | 9/2006 | Leveque et al. | 382/165 |
| 2010/0105102 A1 | * | 4/2010 | Hanes et al. | 435/29 |

FOREIGN PATENT DOCUMENTS

| | | |
|---|---|---|
| FR | 2 667 778 | 4/1992 |
| WO | WO 89/04630 | 6/1989 |

OTHER PUBLICATIONS

English language Derwent Abstract of FR 2 667 778, Apr. 17, 1992.

* cited by examiner

DEVICE FOR USE IN MEASURING AND/OR ANALYSING AT LEAST ONE PARAMETER OF AN EXTERNAL BODY PORTION

This application claims benefit of U.S. Provisional Application No. 60/331,003, filed Nov. 6, 2001, which is herein incorporated by reference.

The present invention relates to a device for use in measuring and/or analyzing at least one parameter of an external portion of a body, such as, for example, the skin, the nails, and/or the hair. Information relating to the parameter may be useful for prescribing and/or determining the effectiveness of various cosmetic treatments of the external portion.

When the external body portion includes skin, the external portion may include skin which has been completely or partially reconstructed artificially. In such an example, the measurement and/or analysis may take place at any moment during the process of reconstruction of the skin. The measurement and/or analysis may be conducted for the purpose of determining certain physicochemical characteristics of the skin, for example.

By way of non-limiting examples, such a device may be used to determine the condition of the stratum corneum, and/or to analyze the secretions, excretions, or odors present at the surface of the skin and/or the hair. The device may further be used to analyze the bioanalytical, bacteriological, and/or enzymatic content of the skin, the nails, and/or the hair.

The substances which may be sampled by the device according to the invention may be in solid form (e.g., dead skin cells, hair cuticles, surface of nails), liquid form (e.g., sebum, water) and/or gaseous form (e.g., volatile and/or odorant compounds).

Such a device may also be used for evaluating mechanical properties of the skin, such as, for example, softness, elasticity and/or microrelief. The microrelief may be characterized, for example, by the number and/or the depth of the wrinkles, including micro-wrinkles, present at the surface of the skin. In a further example, the microrelief may be characterized by the density and/or the size of the pores of the skin.

It is known practice to use sampling devices, such as those in the form of "scrapers" or adhesive elements, intended, for example, to sample dead skin cells at the surface of the skin. Many such devices are made of plastic.

The drawback of conventional devices comes from the fact that some analyses, in particular those involving high temperatures and/or high pressures, cannot be carried out directly on these devices because of their inability to withstand such extreme temperatures and/or pressures.

For example, extreme temperature conditions may be encountered in gas-phase chromatography, where the temperature to which the sample is subjected may range up to 450° C., or even 500° C. High pressure conditions may be encountered in liquid-phase chromatography, where the pressure may range up to 150 bar.

These analysis techniques may be used to qualify and/or quantify one or more elements sampled by the conventional sampling devices. Because the conventional sampling devices may not be able to withstand the analyses, it is often necessary to transfer the sampled substances to a suitable support or into a suitable container that is able to withstand the conditions of elevated temperature and/or pressure. The sampled substances may be transferred by suction, for example, or by other mechanical, physical, and/or chemical means.

This results in tedious manipulations which may cause the loss of part of the substances sampled. Consequently, the measurement may be imprecise.

In addition, the inability of conventional devices to withstand extreme conditions (e.g., temperature, pressure) or conditions linked to an aggressive chemical environment, makes them difficult to clean under conditions such that they may be reliably reused.

Still further, a large number of conventional devices may comprise impurities, such as adhesives, for example, liable to interfere with the measurement.

The above problems are associated with the device described in patent application FR-A-2 667 778. This device makes it possible to circulate a liquid over the skin for the purpose of recovering elements present on the skin's surface. The device comprises joining pieces intended to connect the device to an inlet pipe and to an outlet pipe for the liquid. The device is preferably made of plastic. Other materials, such as ceramic, are mentioned as materials which may be used. However, such a device, when the joining pieces are bonded, cannot be subjected to pressure and temperature conditions as described above, due to the inability of the adhesive to withstand such conditions.

Other conventional devices make it possible to sample fatty substances, such as sebum, present on the hair or at the surface of the skin. For example, patent FR-A-2 368 708 describes the use of a ground glass plate to collect sebum, in particular at the surface of an individual's forehead. The drawback of glass in its solid form relates to the fact that, even when ground, its surface is not rough enough to ensure sufficient trapping of the substances sampled by the surface brought into contact with the portion of skin to be examined. Thus, for example, if dead skin cells were sampled with a glass plate, even a ground glass plate, a large number of these cells would fall off when it was transported between the site at which the sample is taken and the treatment unit in which the device is analyzed. In addition, accidentally passing a finger over the surface of the glass would also cause a large number of the elements sampled to be removed.

U.S. Pat. No. 5,433,214 describes a device intended to quantify the fat and/or the water present at the surface of the skin. According to that document, the device consists of a fine layer of silicon dioxide ($SiO_2$) deposited by printing onto a colored substrate made of paper or PVC. When the layer of $SiO_2$ is in contact with water or fat, it becomes transparent, allowing the color of the substrate to appear.

Such a device, due in particular to the nature of the substrate, and of any other organic element of which it is at least partly made, cannot be subjected to analyses involving high temperature and/or pressure conditions.

The same is true for the device described in U.S. Pat. No. 5,958,339.

Document WO 89/04630 describes a sampling device in the form of a solid element which, according to a preferred embodiment, comprises a trapping material (which may be inorganic) impregnated on a support which may be made of fabric, or of perforated or porous plastic, such as TEFLON. Once again, such a device cannot withstand temperature and pressure conditions as explained above.

The same is true for the device described in U.S. Pat. No. 4,819,645. According to that document, the structure acting as a "trapper" of substances to be sampled consists of a "liquid transfer medium" and a reservoir material dispersed in the "liquid transfer medium". The latter is in the form of an organic gel, such as agarose or PVA. This once again results in a structure incapable of withstanding the pressure and temperature conditions mentioned above.

The present invention may fully or partially obviate one or more limitations of the related art.

The present invention is described by referring to a number of aspects and embodiments. It should be understood that these aspects and embodiments are exemplary and that the invention could be practiced without necessarily having all of the features of the aspects and embodiments described herein.

One aspect of the invention relates to a device that may be used both to sample the substance or substances representative of the parameter to be evaluated, and to directly analyze the substances sampled.

Another aspect of the invention relates to a device capable of withstanding extreme conditions, such as temperature and/or pressure, as encountered, for example, in gas-phase chromatography and/or liquid-phase chromatography devices, or as required so as to allow it to be satisfactorily cleaned.

Yet another aspect relates to a device which may be thoroughly cleaned for the purpose of being reused.

In one aspect, a device for use in measuring and/or analyzing at least one parameter of an external portion of a body may comprise at least one surface configured to be placed in the vicinity of said external portion, wherein said device is either a) configured to be able to be modeled over said external portion and made of a material comprising inorganic material, or b) configured to not be able to be modeled over said external portion and made essentially of at least one inorganic material, wherein when the device is configured to not be able to be modeled, and when material defining the surface is not in at least one of a fibrous form and a particulate form, the surface comprises an inorganic material other than glass.

The at least one parameter may be selected from biological parameters, mechanical parameters, chemical parameters, and physicochemical parameters. Further, the external portion of the body may be selected from the skin, the nails, and the hair.

As used herein, "in the vicinity of" means in contact with or in the immediate area of, such as, for example, proximate to or opposite to. Thus, in the case of an analysis by sampling, the surface may be brought into contact with (e.g., placed up against) the external portion to be analyzed when liquid and/or solid substances are sampled. For substances in the gaseous phase, sampling may take place either with or without contact between the device and the external portion. For example, it may be possible to carry out the sampling of certain substances even when the surface of the device is maintained at a short distance from the external portion.

As used herein, "made essentially of at least one inorganic material" relates to a structure comprising no material other than one or more inorganic materials. It is noted that the device may be reversibly coupled to an auxiliary member, such as, for example, a gripping member, an entrainment member, a rotary member, a measuring member and/or an attaching member, wherein the auxiliary member may be made of materials other than inorganic materials.

When any accessories and instruments that may accompany the device are separated from the device, the device "made essentially of at least one inorganic material" comprises no material other than inorganic material. Materials other than inorganic materials may interfere with a measurement and/or analysis carried out on the device after its application to the external portion or may make the device unsuitable for extreme temperature and/or extreme pressure conditions to which it may be subjected, for example, for the purpose of analysis and/or of cleaning.

The device may be attached, by reversible bonding, for example, to an adhesive support so that the device may be maintained on the skin, for example, for a longer period of time. The adhesive may be configured such that it adheres more to the support than to the device, so that the device may be separated from the support without leaving any adhesive on the device. The device may then undergo an analysis where the device is subjected to extreme temperature and/or extreme pressure conditions.

In one embodiment, when material defining the surface is not in at least one of a fibrous form and a particulate form, the surface may comprise an inorganic material other than metal.

In another embodiment, in particular when the device is configured to not be able to be modeled, the device may have an average thickness of greater than 0.055 mm. In a further embodiment, the device may have an average thickness of greater than 0.1 mm. In a still further embodiment, the device may have an average thickness of greater than 0.5 mm. In yet another embodiment, the device may have an average thickness of greater than 1 mm. In a further embodiment, the device may have an average thickness of greater than 2 mm.

As used herein, "able to be modeled" means capable of being shaped so as to closely match the profile of the external portion to be analyzed when the device is placed up against said external portion, and of maintaining said profile when it is separated from said external portion, so as to form an imprint of said external portion. Stiffening of the material may occur in particular at ambient temperature.

When the device is not in a form able to be modeled, it may be obtained by machining, molding, and/or compacting.

In one aspect, the device may be heat resistant and/or pressure resistant. Such a device may be configured to not be able to be modeled.

As used herein, "heat resistant" means capable of withstanding a temperature of at least 200° C. In one embodiment, the device may also be capable of withstanding a temperature of at least 400° C.

As used herein, "pressure resistant" means capable of withstanding a pressure of at least 20 bar. In one embodiment, the device may also be capable of withstanding a pressure of at least 50 bar. In a further embodiment, the device may also be capable of withstanding a pressure of at least 100 bar.

In one aspect, the device may be configured as a single layer structure.

In another aspect, the device may be made of a ceramic, possibly configured to be able to be modeled, or of an element made of a fibrous, in particular compacted, inorganic material, such as glass wool or rockwool.

The inorganic material constituting the device, when the device is configured to be able to be modeled; may also comprise a ceramic material.

As used herein, "ceramic" is an inorganic, nonmetallic material, obtained by carrying out a heat treatment during the process for the production thereof.

In one aspect, in particular when the device is configured to not be able to be modeled, a) the device may be porous so that the device can be deeply impregnated with a liquid reagent or with a substance in liquid phase or in gaseous phase liable to be present at the surface of the external portion, and/or b) the surface may be rough so as to be able to abrade solid substances from the external portion and to retain said solid substances inside cavities formed between protrusions on said surface.

Solid substances which may be present at the surface of the skin, the hair, and/or the nails include, for example, dead skin cells, cuticles, and dandruff.

The roughness of the surface may correspond to that of an abrasive surface having a grain size ranging from about P 12 to about P 2 500, as defined by the ISO 6344-1, ISO 6344-2, and ISO 6344-3 standards.

At the time of a sampling, using the abrasive properties of the surface of the device, the device may be placed up against the external portion, for example, the skin, and moved over the external portion by rotation or by translation.

The roughness may result from the presence of suitable raised features present on the surface. In one example, the raised features comprise diamonds distributed evenly over the surface. Thus, for an element in the form of a ceramic disk 2 mm thick and 15 mm in diameter, for example, the maximum height of the raised features may be on the order of 1 mm.

By way of example, a disk provided by the company St GOBAIN, under the reference AF997, has been used. By rotating such a structure placed up against the skin, it has been possible to recover between 250 μg and 400 μg of stratum corneum. The rate of rotation of the sampling element was between approximately 50 and 70 rpm.

The liquid or volatile substances present at the surface of the external portion may be substances which are lipophilic or hydrophilic in nature. They may include, for example, sebum and water.

Satisfactory tests have been carried out with structures in the form of alumina disks having various porosities, including, for example, porosities of 10%, 20% and 35%. Such disks were provided by the company St GOBAIN, under the references 054999, 055000, 100360 and 100370. In these tests, the ceramic disk was brought into contact with the skin of the forehead for 10 minutes. The disk was then immersed in a solvent (dichloromethane/methanol). The amount of sebum collected was approximately 80 μg. After concentration, an aliquot portion of the sample was injected into a chromatograph for the purpose of assaying cholesterol and squalene.

The measurement and/or analysis may involve recording at least one magnitude, image, strength, and/or electrical current obtained in response to bringing the device into static or dynamic contact with the external portion to be analyzed.

Alternatively, the measurement and/or analysis may involve sampling substances in liquid, solid, and/or gaseous form, such as, for example, volatile and/or odorant phases, secretions and/or excretions produced by sebaceous or sweat glands, and/or dead skin cells, present at the surface of the external portion.

In a further alternative, the measurement and/or analysis may involve a change in state, for example, a change in color, of reagents contained in the device, when the latter is placed in the vicinity of the external portion.

With the device according to the invention, it may be possible to have information regarding mechanical, biochemical, bacteriological, enzymatic, and/or analytical parameters of the external portion. It also may be possible to make corresponding assessments.

The device, while it is being brought into contact with the external portion, or after it has been brought into static and/or dynamic contact with the external portion, may be the subject of various analyses. This may be a simple observation of the device, which may make it possible to see what has been sampled at the surface of the skin, or to observe a change in state, for example, a change in color, of a reagent contained in the device.

Such an observation may be carried out by any optical or microscopic means. The analysis may be carried out in particular with the naked eye, using a microscope, or using an image analyzer. Other means may also be used.

Thus, for example, the level of acidity of the skin may be evaluated by observing the color of the device, resulting from the change in color of a reagent contained in the device. Alternatively or in addition, the degree of dryness of the skin may be evaluated by counting the dead skin cells sampled and/or by evaluating their size.

Similarly, after the analytical device has been placed in the vicinity of the external portion (e.g., brought into contact with or placed opposite the skin or the hair for a sufficient period of time), the analytical device according to the invention may be subjected to UV, fluorescent, infrared and/or Raman spectrophotometric observation means. Such observation means are particularly suitable for analyzing pieces of stratum corneum sampled by the analytical device. Other observations may also be conducted.

Alternatively, a direct analysis may be carried out using at least one of a normal or reverse gas-phase chromatograph and a normal or reverse liquid-phase chromatograph. The device may also be subjected to X-ray examination for elemental analysis. Such examinations in particular may make it possible to obtain mappings of the analytical parameters of the stratum corneum, for example.

The device may also be used to collect bacteria present on the external portion, such as the skin, for example, for the purpose of determining the bacterial "equipment" of an individual. In this procedure, application of the device to the skin for a predetermined period of time may be followed by seeding onto a culture medium.

The same procedure may be carried out to assess the enzyme content of the external portion. In this procedure, a rough face of the ceramic may be placed up against the skin, for example, and turned so as to recover some stratum corneum, which will then be the subject of the enzymatic analysis.

In addition, as described below, the device may be coupled to instrumentation, such as, for example, a strength sensor, intended to measure the strength required to entrain the device according to a predetermined movement when it is in contact with (e.g., placed up against) the skin. Mechanical properties of the skin, such as its softness, for example, may then be measured. Other properties may also be measured.

Alternatively, such instrumentation may include electrodes capable of measuring the development of certain parameters such as the pH or an electrochemical signal.

In a further alternative, such instrumentation may comprise electrodes coupled, for example, to enzymatic biosensors present in the device, so as to record signals for the purpose, for example, of recording variations in particular parameters.

When the instrumentation is integrated into the device, in particular when the device is in the form in which it is configured to not be able to be modeled, the instrumentation also may be made of inorganic material, such as, for example, one or more metals capable of withstanding high temperature and/or high pressure conditions.

According to one embodiment, the device is made of a nonmetallic inorganic material, with the exception of these sensors and/or other accessory means optionally integrated into the device.

The form of the device may be chosen as a function of the analysis to be carried out and of the surface to be examined. The device may be made, for example, in the form of a block, a disk, one or more slides, or a sheet. In one aspect, the device may have a thickness ranging from about 0.055 mm to about 20 mm, such as from about 0.5 mm to about 10 mm. In another aspect, the device may have a thickness ranging from 0.055 mm to 20 mm, such as from 0.5 mm to 10 mm.

The device may be configured in flexible or nonflexible form depending on the profile of the external portion to which the device is intended to be applied.

In one aspect, the device may be configured in the form of a disk having a diameter ranging from about 0.5 mm to about 50 mm, such as from about 5 mm to about 30 mm. In another aspect, the device may be configured in the form of a disk having a diameter ranging from 0.5 mm to 50 mm, such as from 5 mm to 30 mm.

According to one embodiment, the device may be porous. In a further embodiment, the device may contain at least one reagent capable of reacting with at least one substance present at the surface of said external portion, or in the proximity of the surface of said external portion. In a still further embodiment, the reagent may be sensitive to at least one of pH, urea, aqueous ammonia, albumin, sugar, lipids, and lactic acid.

In one aspect, the device may be reusable. Thus, after being used for an analysis, the device may be cleaned by means of suitable heat and/or chemical treatment for the purpose of further use.

In another aspect, the device may further comprise at least one sensor intended in particular to demonstrate at least one parameter, in particular at least one biochemical parameter and/or at least one mechanical parameter, of said external portion. The at least one biochemical parameter may be selected from protease, phosphatase, catalase, esterase, and glucosidase. Further, the at least one mechanical parameter may be selected from softness, elasticity, and microrelief.

The sensor may be coupled or may be configured to be coupled to at least one of an integrating device and a recording device. Other data acquisition and data storage equipment may also be used.

In one aspect, the device may comprise a machinable ceramic. In a further aspect, the device may be made of a ceramic based on at least one of graphite, silica, alumina, titanium dioxide, iron trioxide, calcium oxide, potassium dioxide, and sodium oxide.

In another aspect, the device may be made of a moldable ceramic material, possibly able to be modeled at ambient temperature. In yet another aspect, the moldable ceramic material may be based on at least one of molten silica, zirconium oxide, silicon carbide, and alumina.

Thus, like a modeling clay, the moldable ceramic material may be applied to the external portion, for example, the skin, and made to match the profile thereof. Such a material may stiffen at ambient temperature. After stiffening, the device may be moved from the vicinity of the external portion. An image of the microrelief of the skin, and in particular of the wrinkles, micro-wrinkles, and/or pores present at the surface of the skin, may be observed on the surface of the device that was brought into contact with the skin. The image thus transferred may then be the subject of optical observation and/or of image analysis. Other analyses may also be performed.

When the device is configured to be able to be modeled, the device also or alternatively may be the subject of analyses involving extreme temperature and/or pressure conditions.

According to another aspect of the invention, a method for selecting a cosmetic treatment to be applied to an external portion of a body, in particular the skin, the nails, or the hair may comprise selecting at least one cosmetic product to be applied to said external portion, wherein the at least one cosmetic product may be selected based on the result of analysis and/or measurement of at least one parameter of said external portion, the result being obtained by using the device according to the present invention. The method may further comprise prescribing the at least one cosmetic product to an individual.

As used herein, "cosmetic product" means any substance or preparation intended to be brought into contact with the various superficial parts of the human body (e.g., epidermis, body hair and hair system, nails, lips, external genital organs) or with the teeth and the buccal mucosa, for the exclusive or main purpose of cleansing them, or of giving them a fragrant smell, of modifying their appearance, and/or of correcting body odors, and/or of protecting them, and/or of maintaining them in good condition. (As set forth in cosmetic directive 76/768/EEC amended).

By way of nonlimiting examples, cosmetic products may include any product intended to reduce the signs of aging of the skin (e.g., wrinkles) and/or the hair; to moisturize the skin; to cleanse, to nourish, and/or to maintain the skin and/or the hair; to deodorize the skin; to prepare the skin for exposure to the sun; to reinforce the elasticity of the skin; and/or to enhance the softness of the skin.

As used herein, "cosmetic treatment" means any treatment by means of a cosmetic product as defined above.

In one aspect, a method of cosmetic treatment of an external portion of a body, in particular the skin, the nails, or the hair, may comprise measuring and/or analyzing at least one parameter of said external portion, wherein said measuring and/or analyzing comprises using the device of the present invention, and depending on the result of said measuring and/or analyzing, applying, to said external portion, at least one cosmetic product intended to have a beneficial action on said parameter.

In another aspect, a method for determining the effectiveness of a cosmetic treatment applied to an external portion of a body, in particular the skin, the nails, or the hair, may comprise measuring and/or analyzing at least one parameter of said external portion, wherein said measuring and/or analyzing comprises using the device of the present invention, depending on the result of said measuring and/or analyzing, performing at least one application, to said external portion, of at least one cosmetic product intended to have a beneficial action on said parameter, and measuring and/or analyzing said parameter again, wherein said measuring and/or analyzing said parameter again comprises using said device.

If, after measuring and/or analyzing said parameter again, the results are nonexistent or insufficient, a different cosmetic treatment may be prescribed, in addition to or as a replacement for the first cosmetic treatment.

Application of the analytical and/or measuring device to the external portion may be done directly by the individual to be tested. Further, the application may be conducted at the individual's home, at a sales outlet, or in a specialized center, for example, at a beauty salon. Other locations may also be used.

When the device is to be "read" by visual analysis, such as, for example, for the purpose of detecting a simple change in color, the "reading" may be done directly by said individual. Such a reading can be facilitated by providing a colored scale with the device.

The individual may then, by any means, pass the observed result on to a professional, either present at the place where the analysis is carried out, or in a remote location. The professional may establish a diagnosis and, where appropriate, may select a cosmetic treatment intended to have an action on the parameter which was the subject of the analysis.

The "reading" of the device can also be done by a professional. The professional may be present at the testing location, such as, for example, a sales outlet or a specialized center. Alternatively, the professional may be in a location remote from the testing location.

In another alternative, when the equipment used to analyze the device is more considerable, the individual may place the device in an envelope and send it to a remote treatment center, where the device may be "read" and where a diagnosis may be established.

In yet another alternative, the individual may scan an image acquired by the device, such as, for example, an image of the relief of the skin, and send it to a remote treatment center. The image may be sent via a communication network, such as the internet, e-mail, and/or parcel delivery service. One or more professionals associated with the remote treatment center may establish a diagnosis and may prescribe, where appropriate, a cosmetic treatment.

In a further aspect, a method for analyzing and/or measuring at least one parameter, in particular biological, mechanical, chemical, or physicochemical parameter, of an external portion of the body, in particular the skin, the nails, or the hair, may comprise placing in the vicinity of said external portion the surface of the device of the present invention, so as to sample at least one substance in the vicinity of a surface of said external portion, moving the device from the vicinity of said external portion (e.g., withdrawing the device from the external portion), and conducting at least one of an analysis and a measurement of the sample, wherein the conducting comprises subjecting the device to a temperature of at least 200° C. and/or a pressure of at least 20 bar. The conducting may comprise performing at least one of a gas-phase chromatography and a liquid-phase chromatography.

In a still further aspect, a method of enabling measuring and/or analyzing of at least one parameter of an external portion of a body may comprise providing the device of the present invention, removably securing an auxiliary member and the device together, and using the auxiliary member to place the device in the vicinity of the external portion so as to sample at least one substance. The auxiliary element may comprise at least one of a gripping element, an entrainment element, and an attaching element.

The term "providing" is used in a broad sense, and refers to, but is not limited to, making available for use, enabling usage, manufacturing, giving, supplying, obtaining, getting a hold of, acquiring, purchasing, selling, distributing, possessing, making ready for use, and/or placing in a position ready for use.

According to an aspect of the invention, a method of enabling measuring and/or analyzing of at least one parameter of an external portion of a body may comprise providing the device of the present invention, and placing the device in the vicinity of the external portion so as to sample a substance.

In another aspect, the method may further comprise receiving information relating to the at least one parameter, wherein receiving information comprises at least one of receiving the device and receiving data from the device.

In yet another aspect, the method may further comprise moving the device from the vicinity of the external portion, and conducting at least one of an analysis and a measurement of the sample. The conducting may comprise subjecting the device to a temperature of at least 200° C. and/or a pressure of at least 20 bar. Further, the conducting may comprise performing at least one of a gas-phase chromatography and a liquid-phase chromatography.

In yet another aspect, a system for use in measuring and/or analyzing at least one parameter of an external portion of a body may comprise the device of the present invention, and an auxiliary member removably secured to the device, wherein the auxiliary member is configured to enable placement of the device in the vicinity of the external portion for sampling at least one parameter of the external portion. The auxiliary member may comprise at least one of a gripping element, an entrainment element, and an attaching element.

The accompanying drawings are included to provide a further understanding of certain aspects of the invention and are incorporated in and constitute part of the specification.

Figure 1:
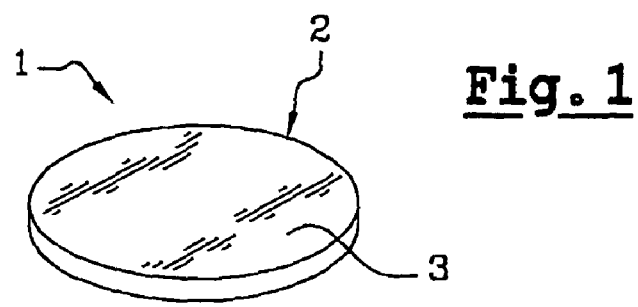
FIG. 1 is a perspective view of a device according to an embodiment of the invention.

The analytical device 1 shown in FIG. 1 is configured in the form of a disk 2 approximately 1 cm in diameter and approximately 4 mm in thickness. The disk is made of a machined ceramic marketed under the commercial reference 902 by the company COTRONICS®. Such a ceramic is made up of a mixture of silica, alumina, titanium dioxide, iron dioxide, calcium oxide, potassium dioxide, and sodium oxide.

The surface 3 of the disk 2 intended to be brought into contact with the skin is rough such that, by placing the surface against the skin and by moving it relative to the skin, dead skin cells are pulled off the skin and trapped by the rough surface 3.

Figure 4:
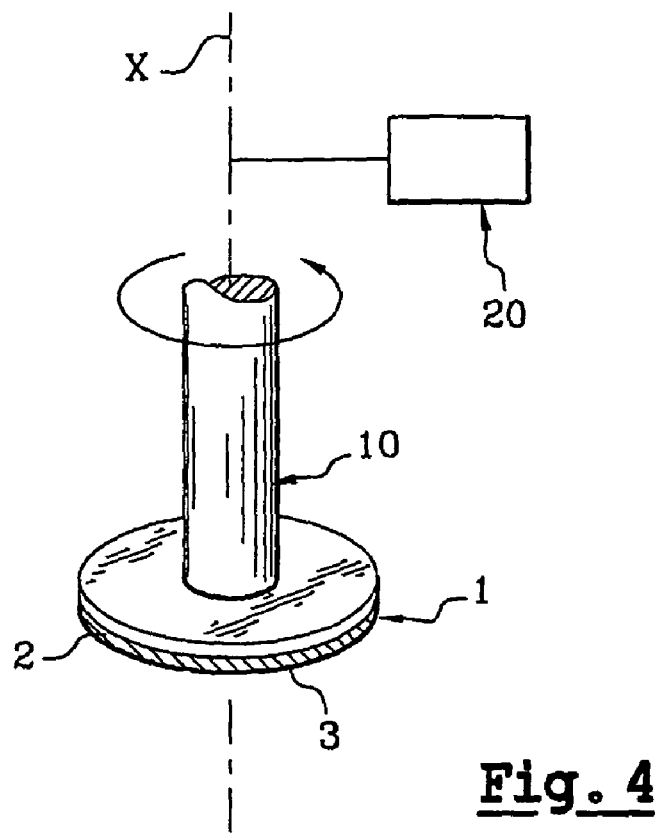
FIG. 4 is a schematic illustrating a method of using an embodiment of the device according to the invention.

The surface 3 may be moved relative to the skin in a way illustrated in FIG. 4, i.e., by rotation around an axis X perpendicular to the plane of said surface 3.

To enable this motion, the measuring device 1 may be mounted, by nonpermanent bonding or by any other reversible means, on a rotary member 10 coupled to a motor 20.

Figure 5:
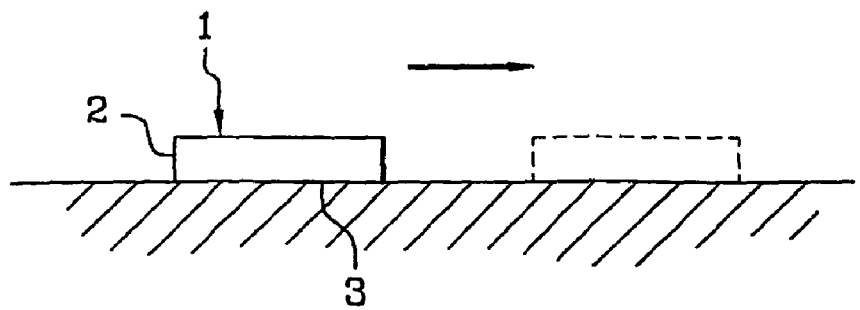
FIG. 5 is a schematic illustrating a method of using another embodiment of the device according to the invention.

Alternatively, the surface 3 of the disk 2 may be moved over the surface of the skin as shown in FIG. 5, i.e., according to a translational movement.

Figure 2:
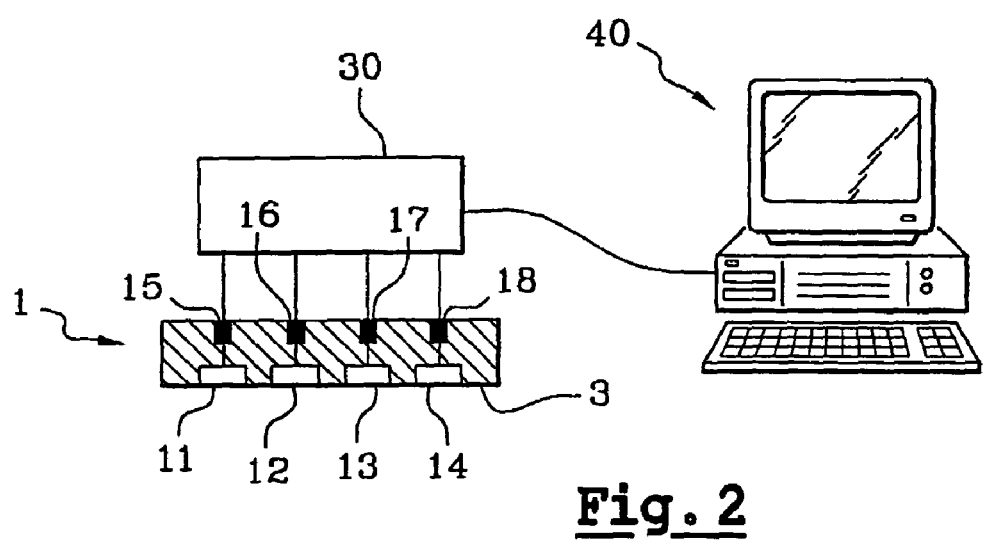
FIG. 2 is a perspective view of a device according to another embodiment of the invention.

In the embodiment of FIG. 2, the ceramic measuring device 1 comprises a plurality of biosensors 11-14, each capable of demonstrating a particular biochemical parameter. The biosensors are disposed in the surface 3 that is intended to be brought into contact with the skin. In the illustrated embodiment, the biosensors 11-14 are sensitive to protease, phosphatase, catalase, and glucosidase, respectively.

Each one of the sensors 11-14 is connected to a respective electrode 15-18 intended to generate corresponding electrochemical signals. The signals generated by the electrodes 15-18 are collected and converted into digital signals by a recording/decoding device 30 connected to a computer 40. This arrangement makes it possible to "monitor" the variations over time of the parameters analyzed.

Figure 3:
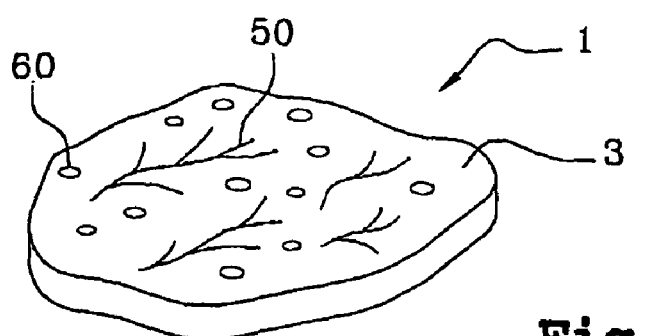
FIG. 3 is a perspective view of a device according to yet another embodiment of the invention.

In the embodiment of FIG. 3, the device 1 comprises a piece of ceramic configured to be able to be modeled, which is applied to the skin and which is matched to the profile of the skin. The ceramic stiffens at ambient temperature. After the device is removed, the surface 3 which was in contact with the skin comprises the image of the wrinkles or fine lines 50 and of the pores 60 present at the surface of the skin. The device is read either visually or by image analysis.

In the embodiment of FIG. 3, the analytical device 1 is made of a moldable ceramic marketed under the reference RESCORE® by the company COTRONICS®.

It will be apparent to those skilled in the art that various modifications and variations can be made to the structure and methodology of the present invention. Thus, it should be understood that the invention is not limited to the examples discussed in the specification. Rather, the present invention is intended to cover modifications and variations.

What is claimed is:

1. A method for analyzing and/or measuring at least one parameter, in particular biological, mechanical, chemical, or physicochemical parameter, of skin, nails, or hair of an external portion of a body, the method comprising:

placing in the vicinity of said external portion the surface of a device, so as to sample at least one substance in the vicinity of a surface of said external portion, wherein the device is for use in measuring and/or analyzing at least one parameter of an external portion of a body, the device comprising at least one surface configured to be placed in the vicinity of said external portion, wherein said device is either
 a) configured to be able to be modeled over said external portion and made of a material comprising inorganic material, or
 b) configured to not be able to be modeled over said external portion and comprising no material other than one or more inorganic materials, wherein when the device is configured to not be able to be modeled, and when material defining the surface is not in at least one of a fibrous form and a particulate form, the surface comprises an inorganic material other than glass;

moving the device from the vicinity of said external portion; and conducting at least one of an analysis and a measurement of the sample, wherein the conducting comprises subjecting the device to a temperature of at least 200° C. and/or a pressure of at least 20 bar.

2. The method of claim 1, wherein the conducting comprises performing at least one of a gas-phase chromatography and a liquid-phase chromatography.

3. A method of enabling measuring and/or analyzing of at least one parameter of an external portion of a body, the method comprising:

providing a device for use in measuring and/or analyzing at least one parameter of an external portion of a body, the device comprising at least one surface configured to be placed in the vicinity of said external portion, wherein said device is either
 a) configured to be able to be modeled over said external portion and made of a material comprising inorganic material, or
 b) configured to not be able to be modeled over said external portion and comprising no material other than one or more inorganic materials, wherein when the device is configured to not be able to be modeled, and when material defining the surface is not in at least one of a fibrous form and a particulate form, the surface comprises an inorganic material other than glass;

placing the device in the vicinity of the external portion so as to sample at least one substance;

moving the device from the vicinity of the external portion; and conducting at least one of an analysis and a measurement of the sample, wherein the conducting comprises subjecting the device to a temperature of at least 200° C. and/or a pressure of at least 20 bar.

4. The method of claim 3, further comprising receiving information relating to the at least one parameter, wherein receiving information comprises at least one of receiving the device and receiving data from the device.

5. The method of claim 3, wherein the conducting comprises performing at least one of a gas-phase chromatography and a liquid-phase chromatography.

* * * * *